US006933137B2

(12) United States Patent
Egen et al.

(10) Patent No.: US 6,933,137 B2
(45) Date of Patent: Aug. 23, 2005

(54) ANIMAL COMPONENT FREE MENINGOCOCCAL POLYSACCHARIDE FERMENTATION AND SEEDBANK DEVELOPMENT

(75) Inventors: Richard C. Egen, Cheyney, PA (US); Lori Ann Fortin, Bethlehem, PA (US); Willie Wei Qiang Sun, Easton, PA (US)

(73) Assignee: Aventis Pasteur, Swiftwater, PA (US)

( * ) Notice: Subject to any disclaimer, the term of this patent is extended or adjusted under 35 U.S.C. 154(b) by 0 days.

(21) Appl. No.: 10/439,878

(22) Filed: May 16, 2003

(65) Prior Publication Data

US 2004/0229319 A1 Nov. 18, 2004

(51) Int. Cl.[7] .......................... C12N 1/20; C12P 21/00; C12P 19/04; C12P 19/26

(52) U.S. Cl. ........................ 435/71.1; 435/84; 435/104; 435/252.1; 435/253.6

(58) Field of Search ......................... 435/71.1, 84, 101, 435/252.1, 253.6

(56) References Cited

U.S. PATENT DOCUMENTS 5,494,808 A 2/1996 Fu

OTHER PUBLICATIONS

Catlin, BW. Nutritional profiles of Neisseria gonorrhoeae, Neisseria . . . , Journal of Infectious Diseases, Aug. 1973, pp. 178–194, vol. 128, Issue 2.

La Scolea LJ Jr. Development of a defined minimal medium for the growth of Neisseria gonorrhoeae. Applied Microbiology, Jul. 1974, pp. 70–76, vol. 28, Issue 1.

Fu, et al. Recent Advances in the large scale fermentation of Neisseria meningitidis . . . , Bio/Technology, Feb 1995, pp. 170–174, vol. 13.

*Primary Examiner*—Herbert J. Lilling
(74) *Attorney, Agent, or Firm*—Thomas J. Bordner

(57) ABSTRACT

Animal-free meninge fermentation media and process is developed based upon use of a chemically defined medium. To improve polysaccharide production, fed-batch fermentation is examined using different feed solutions and feeding strategies. A feed solution containing glucose, amino acids, and trace metal elements produces Group A polysaccharide at approximately 3 times the level observed with batch fermentation. This process is used successfully to produce polysaccharides of *N. meningitidis* serotypes, A, C, Y and W-135 and is run reproducibly at the 20 L scale and can be scaled to 400 L or more.

19 Claims, No Drawings

ANIMAL COMPONENT FREE MENINGOCOCCAL POLYSACCHARIDE FERMENTATION AND SEEDBANK DEVELOPMENT

BACKGROUND OF THE INVENTION

1. Field of the Invention

This invention relates to the field of vaccine preparation and, in particular, fermentation of *Neisseria* bacteria, particularly *N. meningitidis*, for the production of polysaccharide for use in vaccines.

2. Summary of the Related Art

*N. meningitidis* causes both endemic and epidemic disease, principally meningitis and meningococcemia. As a result of the control of *Haemophilus enfluenzae* type b infections, *N. meningitidis* has become the leading cause of bacterial meningitis in children and young adults in the United States (US), with an estimated 2,600 cases each year. (Recommendation of the Advisory Committee on Immunization Practices (ACIP). "Control and prevention of meningococcal disease and control and prevention of serogroup C meningococcal disease: evaluation and management of suspected outbreaks." MMWR 46: No. RR-5, 1997 6 (hereinafter "ACIP"); CDC 1, Laboratory-based surveillance for meningococcal disease in selected areas—United States, 1989–1991, MMWR 42: No SS-2, 1993 (hereinafter "CDC 1").) The case-fatality rate is 13% for meningitis disease (defined as the isolation of *N. meningitidis* from cerebrospinal fluid) and 11.5% for persons who have *N. meningitidis* isolated from blood (ACIP, CDC 1) despite therapy with antimicrobial agents (e.g., penicillin) to which US strains remain clinically sensitive. (ACIP).

Based on multistate surveillance conducted during 1989 to 1991, serogroup B organisms accounted for 46% of all cases and serogroup C for 45%; serogroups W-135 and Y and strains that could not be serotyped accounted for most of the remaining cases. (ACIP, CDC 1) Recent data indicate that the proportion of cases caused by serogroup Y strains is increasing. (ACIP) In 1995, among the 30 states reporting supplemental data on culture-confirmed cases of meningococcal disease, serogroup Y accounted for 21% of cases. (CDC. Serogroup Y Meningococcal Disease—Illinois, Connecticut, and Selected Areas, United States, 1989–1996. MMWR 46: Vol. 45, 1010–1013, 1996 (hereinafter "CDC 2").) Serogroup A, which rarely causes disease in the US, is the most common cause of epidemics in Africa and Asia. A statewide serogroup B epidemic has been reported in the US. (CDC. Serogroup B meningococcal disease—Oregon 1994. MMWR 44: 121–124, 1995 (hereinafter "CDC 3").) *N. meningitidis* vaccines comprise group specific polysaccharide antigens. Several discoveries impacted the future of meningococcal polysaccharide vaccines and demonstrated the significance of anti-capsular antibodies in protection. (Frasch, "Meningococcal vaccines; past, present and future," in *Meningococcal Disease*, ed. K. Cartwright. John Wiley and Sons Ltd, 1995.) In the late 1930s, serogroup-specific antigens of meningococcal serogroups A and C were identified as polysaccharides. (CDC 3) During the mid 1940s, investigators demonstrated that the protection of mice by anti-serogroup A meningococcal horse serum was directly related to its content of anti-polysaccharide antibodies. (Frasch) Meningococcal polysaccharide vaccines were first demonstrated to be immunogenic in humans by Gotschlich and his co-workers in the 1960s when immunization of US Army recruits with serogroup A and C polysaccharides induced protective antibodies. Id. The investigators recorded a significantly reduced acquisition rate of serogroup C carriage among vaccinated recruits compared with unvaccinated individuals. Id.

*Meningitidis* polysaccharide manufacture requires fermentation of *N. meningitidis*. Current good manufacturing practice (cGMP) imposes several criteria to medium development for microbial fermentation for the production of biologics. Ideally, the medium should contain only essential components, be easily prepared in a reproducible manner, and support robust high-cell density culture. A chemically defined medium is inherently more reproducible than a complex medium. Furthermore, a chemically defined medium enables discrete analysis of the effect of each component and strict control of medium formulation through identity and purity testing of raw materials. Finally, the fermentation medium should support the cultivation of the microorganism in question to high-cell density to improve volumetric productivity and to generate a final culture whose composition and physiological condition is suitable for downstream processing.

Catlin [*J. Inf. Dis.* 128:178–194, 1973], described a complex chemically defined medium named NEDF, containing approximately 54 ingredients, including all twenty naturally occurring amino acids, for growth of *Neisseria*. In addition, Catlin described a medium called MCDA containing 18 ingredients (in mM: NaCl, 100; KCl, 2.5; $NH_4Cl$, 7.5; $Na_2HPO_4$, 7.5; $KH_2PO_4$, 1.25; $Na_3C_6H_5O_7.2H_2O$, 2.2; $MgSO_4.7H_2O$, 2.5; $MnSO_4.H_2O$, 0.0075; L-glutamic acid, 8.0; L-arginine.HCl, 0.5; glycine, 2.0; L-serine, 0.2; L-cysteine $HCl.H_2O$, 0.06; sodium lactate, 6.25 mg of 60% syrup/mL of medium; glycerin, 0.5% (v/v); washed purified agar, 1% (wt/vol) $CaCl_2.2H_2O$, 0.25; $Fe_2(SO_4)_3$, 0.01) which was reported to support growth of *Neisseria meningitidis* on agar. The ability of MCDA to support growth in liquid medium (that is absent addition of agar) was not reported. La Scolea et al., [*Applied Microbiology* 28:70–76, 1974] reported on a defined minimal medium named GGM for the growth of *Neisseria gonorrhoeae*. The medium contained minimal salts, eight amino acids, two nitrogen bases, vitamins, coenzymes, metabolic intermediates and miscellaneous components. La Scolea et al. reported growth of this strain to an optical density of 400 Klett units. An absorbance of 1 at 600 nm is considered equivalent to 500 Klett units [see Gerhardt et al., *Manual of Methods for General Bacteriology,* 1981, ASM., p. 197]. Therefore, the maximum reported growth density achieved by LaScolea et al., was less than about one (1) absorbance unit.

SU 1750689 A1 described a method for preparing polysaccharide-protein vaccines against *Neisseria meningitidis* B. A defined medium was described having the following composition, g/L:

| | |
|---|---|
| Sodium L-glutamate | 1.30 ± 0.10 |
| L-cysteine hydrochloride | 0.03 ± 0.01 |
| Potassium chloride | 0.09 ± 0.01 |
| Sodium chloride | 6.00 ± 1.00 |
| Magnesium sulfate heptahydrate | 0.06 ± 0.01 |
| Ammonium chloride | 1.25 ± 0.01 |
| Disubstituted sodium phosphate dodecahydrate | 2.50 ± 0.20 |
| Trisubstituted sodium citrate | 0.50 ± 0.10 |
| Glucose | 1.60 ± 0.20 |

In this medium, it is reported that *Neisseria* may be cultured to a final optical density of 1.5±0.2 on the FEK- 56M scale. This is an unfamiliar scale for optical density determination. However, based on the available carbon sources in the above noted medium, it is predictable that the maximum absorbance achievable would be in the range of about 1.5 absorbance units.

U.S. Pat. No. 5,494,808 reports a large-scale, high-cell density (5 g/L dry cell weight, and an optical density of between about 10–13 at 600 nm) fermentation process for the cultivation of *N. meningitidis*. This patent disclose the following medium (called "MC.6") for culturing *Neisseria meningitidis* for isolation of OMPC ("Outer Membrane Protein Complex") (all values in mg/L):

| | |
|---|---|
| NaCl | 5800 |
| $K_2HPO_4$ | 4000 |
| $NH_4Cl$ | 1000 |
| $K_2SO_4$ | 1000 |
| Glucose | 10,000 |
| L-Gutamic Acid | 3900 |
| L-Arginine | 150 |
| Glycine | 250 |
| L-Serine | 500 |
| L-Cysteine.HCl | 100 |
| $MgCl_2.6H_2O$ | 400 |
| $CaCl_2.2H_2O$ | 28 |
| Fe(III) Citrate | 40 |

MENOMUNE® A/C/Y/W-135, Meningococcal Polysaccharide Vaccine, Groups A, C, Y and W-135 Combined, for subcutaneous use, is a freeze-dried preparation of the group-specific polysaccharide antigens from *Neisseria meningitides,* Group A, Group C, Group Y and Group W-135. *N. meningitidis* are cultivated with Mueller Hinton agar1 and Watson Scherp2 media. The purified polysaccharide is extracted from the *Neisseria meningitidis* cells and separated from the media by procedures which include centrifugation, detergent precipitation, alcohol precipitation, solvent or organic extraction and diafiltration.

SUMMARY OF THE INVENTION

Animal-free meninge fermentation media and process was developed based upon use of a chemically defined medium. To improve polysaccharide production, fed-batch fermentation was examined using different feed solutions and feeding strategies. A feed solution containing glucose, amino acids, and trace metal elements produces Group A polysaccharide at approximately 3 times the level observed with batch fermentation. This process is successfully applied to serotypes A, C, Y and W-135. This process runs reproducibly at the 20 L scale and can be scaled to 400 L or more.

The foregoing is summarizes certain embodiments of the invention (which is more completely described below) and, therefore, should not be construed as limiting the invention in any manner. All patents, patent applications, and other publications referred to in this specification are hereby incorporated by reference in their entirety.

DETAILED DESCRIPTION OF THE INVENTION

In a first aspect, the present invention comprises new compositions of matter for fermenting *Nisseria*. This composition is particularly useful in fermenting *Nisseria* to produce a vaccine. The compositions of the invention comprise aqueous compositions of matter comprising a solution resulting from dissolving in water the compounds listed in one of the following tables at the indicated concentrations (g/L)±10%:

TABLE 1a

| Modified Watson Scherp Medium I (MWSM I) | |
|---|---|
| Sodium phosphate, dibasic | 2.500 |
| Soy peptone | 5–30 |
| Monosodium Glutamate | 5.000 |
| Potassium Chloride | 0.103 |
| Magnesium sulfate | 0.732 |
| L-Cysteine | 0.016 |
| Glucose | 11.250 |

TABLE 1b

| Modified Watson Scherp Medium II (MWSM II) | |
|---|---|
| Sodium phosphate, dibasic | 2.500 |
| Soy peptone | 5–30 |
| Monosodium Glutamate | 5.000 |
| Potassium Chloride | 0.103 |
| Magnesium sulfate | 0.732 |
| Glucose | 11.250 |

TABLE 2a

| Meningitidis Chemically Defined Medium I (MCDM I) | |
|---|---|
| Glucose | 10.00 |
| Soy Peptone | 5–30 |
| Sodium Chloride | 5.80 |
| Potassium Sulfate | 1.00 |
| Potassium Phosphate, dibasic | 4.00 |
| L-Glutamic Acid | 5.00 |
| L-Arginine | 0.30 |
| L-Serine | 0.50 |
| L-Cysteine | 0.23 |
| Magnesium Chloride | 0.19 |
| Calcium chloride | 0.021 |
| Ferrous Sulfate | 0.002 |

TABLE 2b

| Meningitidis Chemically Defined Medium II (MCDM II) | |
|---|---|
| Glucose | 10.00 |
| Soy Peptone | 5–30 |
| Sodium Chloride | 5.80 |
| Potassium Sulfate | 1.00 |
| Potassium Phosphate, dibasic | 4.00 |
| Magnesium Chloride | 0.19 |
| Calcium chloride | 0.021 |
| Ferrous Sulfate | 0.002 |

We have surprisingly found that $NH_4Cl$ (employed in prior art media) is not readily consumed during *Nisseria* fermentation and is possibly even deliterious. In some experiments, polysaccharide yield is roughly 20–50% greater when $NH_4Cl$ is omitted from the media. Accordingly, we omit this component and surprisingly find that polysaccharide yield is improved. Therefore, the present invention provides a fermentation composition wherein the composition omits $NH_4Cl$, and an improved method of fermenting *Nisseria* in a fermentation composition wherein the composition omits $NH_4Cl$. More preferably, however, the ammonium chloride nitrogen source is replaced with a soy peptone as a nitrogen source. As known by those skilled in the art, soy peptone is enzymatically hydrolyzed soy refined to remove impurities. Preferably 5–30 g/L of soy peptone is used. More preferably, 10–15 g/L is used in the fermentation composition. Among the soy peptone's that can be used in the compositions of the present invention are SE50MAF-UF, Freetone A-1, HSP-A, and HY Soy UF. In one preferred embodiment, the soy peptone is HSP-A (Nutricepts, Inc.; Minneapolis, Minn.). HSP-A has the following composition:

TABLE 4

Soy Peptone Composition

| Flowable spray dried powder | Yes |
|---|---|
| Color | Light Tan |
| Protein | 51% |
| Amino Nitrogen | 3% |
| Total Nitrogen | 8% |
| AN/TN ratio | .38 |
| Ash | <10% |
| Moisture | <8% |
| pH | 6.5 |
| Sodium | 1% |
| Potassium | 4% |

TABLE 5

Amino Acid Profile (mg/g) of Soy Peptone

| Amino Acid | Free | Total |
|---|---|---|
| ASP | 6 | 45 |
| SER | 9 | 30 |
| GLU | 15 | 85 |
| GLY | 2 | 20 |
| HIS | 6 | 15 |
| ARG | 14 | 40 |
| THR | 5 | 20 |
| ALA | 5 | 20 |
| PRO | 3 | 25 |
| CYS | NA | 5 |
| TYR | 5 | 15 |
| VAL | 8 | 20 |
| MET | 4 | 5 |
| LYS | 16 | 30 |
| ILE | 9 | 20 |
| LEU | 19 | 30 |
| PHE | 11 | 20 |
| TOTAL | 137 | 445 |

MCDM I differs from prior art MCDM in that a soy peptone replaces $NH_4Cl$ as a nitrogen source. MCDM II differs from MCDM I in that the amino acids (other than those contributed by the soy peptone) have been removed from the composition; it is expected that the amino acids supplied by the soy peptone are sufficient to sustaain *Nisseria* growth.

Similarly, MWSM I differs from prior art MWSM in that a soy peptone replaces $NH_4Cl$ as a nitrogen source. MWSM II differs from MWSM I in that the amino acids (other than those contributed by the soy peptone) have been removed from the composition; it is expected that the amino acids supplied by the soy peptone are sufficient to sustaain *Nisseria* growth.

The components of the foregoing compositions are commercially available and the compositions can be routinely made by simply dissolving the components in water.

As mentioned, the compositions according to the invention are useful for *Nisseria* fermentation, especially for the production of vaccines, particularly vaccines comprised of *Nisseria* polysaccharides, and more particularly of *Nisseria* polysaccharides of serotypes A, C, Y and W135, e.g., MENOMUNE®.

In another aspect, the invention comprises a method of fermenting *Nisseria* in animal-free media. Any of the media of the invention can be employed. As used herein, the term Animal-Free *Nisseria* Medium ("AFNM") refers to any of MWSM I, MWSM II, MCDM I, and MCDM II. In one embodiment, the method comprises (a) fermenting *Neisseria* in AFNM on one or more seed stages followed by (b) fermenting *Neisseria* in AFNM as the base medium and feed solution. Preferably, MCDM I is the medium used in all stages of the method. Preferably, the scale of each subsequent fermentation in the method is larger than the previous fermentation.

The parameters employed in the method of the invention (e.g., number of seed stages, level of growth at which fermentation is moved from one fermentor to the next, feed rate of feed solution, etc.) are dependent on a number of factors, including the growth characteristics of the strain and batch of *Nisseria* used (which will vary from strain to strain and batch to batch), the type of equipment employed, work schedules, etc. Suitable parameters include those provided in this specification but may vary significantly. Nevertheless, the state of the art is such that it would require no more than routine experimentation for one of ordinary skill in the fermentation art to determine suitable fermentation parameters useful and, indeed, optimal in the method of the invention under the particular circumstances the artisan finds himself.

In one embodiment, the method comprises:
inoculating a vial (e.g., 1 ml) of *Neisseria* to a first flask (e.g., 1 L) containing AFNM medium (e.g., 220 ml);
cultivating the flask (e.g., in a shaker at 36±1° C., 250 rpm for 4–8 hours) to form a seed culture;
transferring (e.g., at OD of about 2) seed culture (e.g., about 10%) to one or a plurality of second flasks (e.g., three 2.8 L flasks) containing AFNM (e.g., 700 ml);
fermenting the contents of the second flask(s) (e.g., at pH 6.8±0.2, temperature 36±1° C., DO 30%, airflow at constant 15 L/min; 2.5M phosphoric acid and 2.5M sodium hydroxide can be used for pH control and 30% Dow 1520 antifoam solution to control foaming);
transferring the contents of the second flask(s) (e.g., at OD between 3–6) aseptically to a fed-batch fermentor (e.g., 400 L fed-batch fermentor) where AFNM is the fermentation base medium (e.g., at pH 6.8±0.2, temperature 36±1° C., DO 30%, with agitation 250–270 rpm, airflow gradually increase to maximum 300 L/min and then gradually increasing back pressure to 8–12 psi to maintain DO); and
feeding AFNM solution into the fermentor (e.g., when glutamate reaches about 2 g/L),
preferably at rate of 5.6 L/hr for first 2 hours feeding and then increase to 7.8 L/hr.

In further aspect, the invention comprises a method of producing *Neisseria* polysaccharide comprising fermenting *Neisseria* according to the any of the methods described above and harvesting the polysaccharide. Typical harvest is done when hourly increase in OD slows and growth reaches stationary phase. Methods of harvesting *Neisseria* polysaccharide are known to those skilled in the art. In a preferred embodiment, the use of a fed-batch fermentor, wherein some or all nutrients are supplied continuously or intermittantly and all products havested at the end of fermentation, results in a significant increase in polysaccharide production.

The following Examples are provided for illustrative purposes only and are not intended to limit the invention in any manner. Those skilled in the art will recognize that variations and modifications of the following Examples may be employed without deviating from the spirit or literal scope of the invention.

EXAMPLES

Unless otherwise indicated, the composition of the MCDM used in the following experiments was the same as MCDM I except that 1 g/L of $NH_4Cl$ was used in place of soy peptone.

Example 1

Fed Batch Animal-Free Fermentation Process Development

Fed-batch fermentation is examined using various feed solutions and feeding under different growth conditions. Fed-batch fermentation produces much higher polysaccharide levels than batch fermentation. It is found that glucose residual remained high at the end of fermentation in subsequent fed-batch fermentations when 200 g/L of glucose is used in the feed solution. Therefore, 100 g/L and 50 g/L of glucose in feed solutions are compared. When 50 g/L of glucose is used, low glucose residual is obtained at end of fed-batch fermentation while polysaccharide remains relatively unchanged. Thus, 50 g/L of glucose concentration is used in the feed solution. Final feed solution components are listed in Table 6.

TABLE 6

| Feed Solution Components (g/L) | |
|---|---|
| Glucose | 50 |
| Glutamic acid | 50 |
| Arginine | 3 |
| Serine | 3 |
| Cysteine | 2 |
| $NH_4Cl$ | 10 |
| $MgCl_2$ | 2 |
| $CaCl_2$ | 0.14 |
| $FeSO_4$ | 0.02 |

Example 2

Animal-Free Medium and Process Improvement: Poor Utilization of Ammonium Ion It is noticed that ammonium ion residual remained relatively constant due to minimal consumption. 2-L fermentations are carried out in order to examine the effect of $NH_4Cl$ on both polysaccharide production and cell growth in either the base medium and/or feed solution. Table 7 lists an average of maximum $OD_{600}$ and polysaccharide from duplicate fermentations for each condition. Higher levels of PS are observed when $NH_4Cl$ is removed from both fermentation medium and feed solution. A similar result is observed at the 400-L scale. Elimination of $NH_4Cl$ from both the base medium and feed solution improves polysaccharide yield and growth compared to inclusion of ammonium only in the base medium. Both maximum polysaccharide (393 mg/L) and growth (OD 5.5) without $NH_4Cl$ in the medium are higher than with $NH_4Cl$ in the medium (PS 269 mg/L and OD 4.5).

TABLE 7

Effect of $NH_4Cl$ in MCDM† and/or feed solution on growth and polysaccharide production at 2L batch fermentation for group C (079C72)

| $NH_4Cl$ | *Max. OD | *Max. PS (mg/L) |
|---|---|---|
| Base MCDM & Feed | 9.1 | 377 |
| Base MCDM only | 8.1 | 403 |
| No $NH_4Cl$ | 7.9 | 447 |

Average of duplicate experiments

Example 3

Nitrogen Source Screen in Watson Scherp Medium

Since inorganic nitrogen as $NH_4Cl$ is removed, the effect of alternative soy-based organic nitrogen sources on growth and polysaccharide production is examined. Experiments are performed with Watson Scherp medium, the current manufacturing standard, and nitrogen sources Freetone A-1, HSP-A, SE50MAF-UF are selected for study. Testing is done in shake flasks and 2-L batch fermentations with Watson Scherp medium, in which casamino acids are replaced on a nitrogen content basis, by each soy-based nitrogen source as shown in Table 8. Table 9 lists average maximum OD and polysaccharide from duplicate fermentations for each condition Average maximum OD 7.9 and PS 468 mg/L are obtained with Freetone A-1; average maximum OD 11.2 and PS 510 mg/L with HSP-A; and average maximum OD 7.8 and PS 491 mg/L with SE50MAF-UF. These results show polysaccharide yield from both HSP-A and SE50MAF-UF is higher than that from Freetone A-1. Therefore HSP-A and SE50MAF-UF are chosen for further testing.

TABLE 8

| Watson Scherp with different organic nitrogen sources (g/L) | |
|---|---|
| Sodium phosphate, dibasic | 2.500 |
| Freetone A-1/SE50MAF-UF/HSP-A | 16.76/24.96/27.8 |
| Monosodium Glutamate | 5.000 |
| Potassium Chloride | 0.103 |
| Magnesium sulfate, crystals | 0.732 |
| L-Cysteine HCl Monohydrate | 0.023 |
| Glucose | 11.250 |

TABLE 9

Effect of nitrogen source on growth and Polysaccharide production 2L scale batch fermentation for group Y

| Nitrogen | Ave. Max. OD | Ave. Max. PS (mg/L) |
|---|---|---|
| Freetone A-1 | 7.9 | 468 |
| HSP-A | 11.2 | 510 |
| SE50MAF-UF | 7.8 | 491 |

A similar batch fermentation experiment is performed in which the two best nitrogen sources from the previous work are compared to the current nitrogen source standard, HY Soy UF. Table 10 lists average maximum OD and polysaccharide from duplicate fermentations for each condition. Maximum OD 7.0 and PS 378 mg/L are obtained with HY Soy UF; average maximum OD 9.5 and PS 602 mg/L with HSP-A; and, average maximum OD 7.8 and PS 595. mg/L with SE50MAF-UF. Fermentation results show that both cell growth and polysaccharide yield from both HSPA and SE50MAF-UF is higher than that from HY Soy UF.

TABLE 10

Effect of nitrogen on growth and polysaccharide production 2L scale batch fermentation for group Y (079C165)

| Nitrogen | Ave. Max. OD | Ave. Max. PS (mg/L) |
| --- | --- | --- |
| HY SOY* | 7.0 | 378 |
| HSP-A | 9.5 | 602 |
| SE50MAF-UF | 7.8 | 595 |

Data from one fermentation

Interestingly, glucose and glutamate are utilized to exhaustion in those fermentations containing HSP-A. Previous work with all *meningitidis* serogroups and MCDM type media result in variable growth and polysaccharide production. One characteristic of those fermentations is variable and incomplete utilization of glucose and glutamate substrates. To our surprise, fermentations containing HSP-A as the nitrogen source totally consume the glucose and glutamate and as a likely outcome resulted in higher levels of both cell growth and polysaccharide production. This characteristic has been shown to be highly reproducible at both 2-L and 300-L scale fermentations. Other nitrogen sources do not exhibit this characteristic. Thus, HSP-A is the preferred nitrogen source.

Example 4

MCDM/HSP-A Development

It is found that HSP-A nitrogen source promotes the best growth and stimulates the highest polysaccharide production in Watson Scherp medium. Since $NH_4Cl$ is shown to cause variable results with respect to growth and polysaccharide production in minimal chemically defined medium (MCDM), the decision is made to substitute HSP-A for ammonium on a nitrogen basis in that medium. In that way it could be determined whether an organic nitrogen source was more acceptable for growth and/or polysaccharide production in *Neisseria meningitidis*. Both MCDM and MCDM/HY Soy, in which HY Soy replaces $NH_4Cl$ on a nitrogen basis, are used as controls. 2×2 L fermentations for each condition are performed. Table 11 lists average maximum OD and polysaccharide from duplicate fermentations for each condition. Average maximum OD 6.4 and PS 234 mg/L with MCDM; average maximum OD 6.7 and PS 199 mg/L with MCDM/HY Soy; and average maximum OD 7.1 and PS 288 mg/L with MCDM/HSP-A are obtained. These results show that MCDM/HSP-A resulted in the best polysaccharide yield and supported the highest growth.

TABLE 11

Effect of nitrogen source on growth and polysaccharide production 2L scale batch fermentation for group Y (079C191)

| Nitrogen | Ave. Max. OD | Ave. Max. PS (mg/L) |
|---|---|---|
| MCDM | 6.4 | 234 |
| MCDM/HY Soy | 6.7 | 199 |
| MCDM/HSP-A | 7.1 | 288 |

HSP-A concentration is varied in MCDM medium in order to examine the effect of HSP-A concentration on growth and polysaccharide production. Table 12 lists average maximum OD and polysaccharide from duplicate fermentations for each condition. Average maximum OD was 6.4 and PS 226 mg/L with 3.2 g/L of HSP-A; average maximum OD 10.4 and PS 346 mg/L with 10 g/L of HSP-A; and average maximum OD 11.4 and PS 317 g/L with 28 g/L HSP-A. These results indicate that 10 g/L of HSP-A maximized polysaccharide production. Therefore, 10 g/L of HSP-A is used in MCDM medium for further experimentation.

TABLE 12

Effect of HSP-A concentration on growth and polysaccharide production at 2L fermentation scale for group Y (087C4)

| HSP-A conc. | Ave. Max. OD | Ave. Max. PS (mg/L) |
|---|---|---|
| 3.2 g/L | 6.4 | 226 |
| 10 g/L | 10.4 | 346 |
| 28 g/L | 11.4 | 317 |

To examine whether MCDM/HSP-A is suitable for other serotypes, 2 L fermentations for group A, C, W135 and Y are performed. Table 13 lists average maximum OD and polysaccharide from duplicate fermentations for each serotype except for group Y, for which only a single fermentation is performed. Average maximum OD 11.1 and PS 745 mg/L are obtained for group A; average maximum OD 10.4 and PS 453 mg/L for group C; and, average maximum OD 11.2 and PS 684 mg/L for group W135. For group Y, maximum OD 12.5 and PS 466 mg/L are observed in a single fermentation. These results show that MCDM/HSP-A is suitable for growth and polysaccharide production by all 4 serotypes. Since all serogroups exhibit similar behavior in MCDM/HSP-A medium (Table 13), it is felt that a single serogroup could be used for sets of experiments targeting process improvement, and likewise that those serogroups could be used interchangeably between sets of experiments, as subsequently demonstrated.

TABLE 13

Application of MCDM/HSP-A to all four serotypes A, C, W135 and Y at 2L fermentation scale (087C23)

| Serotype | Ave. Max. OD | Ave. Max. PS (mg/L) |
|---|---|---|
| A | 11.1 | 745 |
| C | 10.4 | 453 |
| W135 | 11.2 | 684 |
| Y* | 12.5 | 466 |

*For group Y, only one fermentor was run.

Example 5

Fed-Batch Fermentation with MCDM/HSP-A

To further increase polysaccharide yield, fed-batch fermentation is examined. Glutamate concentration is increased to 6 g/L from 5 g/L since it is observed that glutamate is exhausted earlier than glucose during the fermentation. Table 14 lists average maximum OD and polysaccharide from duplicate fermentations for each condition with Serogroup A. Average maximum OD 11.0 and PS 1075 are obtained by batch fermentation. Average maximum OD 14.2 and PS 1424 mg/L are observed with fed-batch fermentation with MCDM feed solution 5 as listed in Table 15. And, average maximum OD 19.5 and PS 1330 mg/L are obtained for fed-batch fermentation with HSP-A feed solution 1, as listed in Table 16. These results show that fed-batch fermentation with MCDM feed solution produces the best polysaccharide yield and also supports very high growth. Final specific product yields (i.e., maximum yield divided by maximum OD) for batch, MCDM feed and HSP-A feed are 97.7, 100.3 and 68.2, respectively.

TABLE 14

Effect of fed-batch fermentation on growth and polysaccharide production at 2 L scale for group A (087C43)

| Fermentation | Ave. Max. OD | Ave. Max. PS (mg/L) | Specific Yield (mg/L · OD) |
|---|---|---|---|
| Batch | 11.0 | 1075 | 97.7 |
| MCDM Feed | 14.2 | 1424 | 100.3 |
| HSP-A Feed | 19.5 | 1330 | 68.2 |

TABLE 15

MCDM feed solution components

| Dextrose | 75.00 | g/L |
|---|---|---|
| Monosodium Glutamate | 37.500 | g/L |
| L-Arginine Monohydrate | 3.00 | g/L |
| L-Serine | 3.00 | g/L |
| L-Cysteine | 2.00 | g/L |
| Magnesium Chloride.6H2O | 2.00 | g/L |
| Calcium Chloride Dihydrate | 0.15 | g/L |
| Ferrous Sulfate.7Hydrate | 0.02 | g/L |

TABLE 16

HSP-A/Watson Scherp feed solution components

| Dextrose | 75.00 | g/L |
|---|---|---|
| HSP-A | 185.00 | g/L |
| Ferrous Sulfate | 0.0468 | g/L |
| Potassium Chloride | 0.75 | g/L |
| L-Cysteine HCl Monohydrate | 0.45 | g/L |
| Monosodium Glutamate | 37.50 | g/L |

For group C experiments two feed regimes, MCDM feed solution or MCDM feed supplemented with HSP-A (as indicated in Table 17) are compared. In order to match the glucose and glutamate consumption rates observed in previous fermentations, MCDM feed 5 components are increased 1.5-fold in the feed solution. As shown in Table 18, average maximum OD 15.4 and PS 560 mg/L are obtained by batch fermentation; average maximum OD 23 and PS 926 mg/by fed-batch fermentation with MCDM feed solution 6; and average maximum OD 30.7 and PS 908 mg/L by fed-batch fermentation with MCDM/HSP-A feed solution. These results indicate that fed-batch fermentation with MCDM feed solution produces the highest polysaccharide yield and also provides the highest PS specific production. The polysaccharide yield from fed-batch fermentation is much higher than that from batch fermentation for both groups A (previous experiment) and C.

TABLE 17

MCDM feed solution components

| Dextrose | 112.5 | g/L |
|---|---|---|
| Monosodium Glutamate | 56.25 | g/L |
| L-Arginine Monohydrate | 4.50 | g/L |
| L-Serine | 4.50 | g/L |
| L-Cysteine | 3.00 | g/L |
| Magnesium Chloride.6H2O | 3.00 | g/L |
| Calcium Chloride Dihydrate | 0.23 | g/L |
| Ferrous Sulfate.7Hydrate | 0.03 | g/L |
| HSP-A (supplement experiment) | 90.00 | g/L |

TABLE 18

Effect of fed-batch fermentation on growth and polysaccharide production at 2L scale for group C (087C76)

| Fermentation | Ave. Max. OD | Ave. Max. PS (mg/L) | Specific yield (mg/L · OD) |
|---|---|---|---|
| Batch | 15.4 | 560 | 36.4 |
| MCDM Feed | 23.0 | 926 | 40.3 |
| HSP-A Feed | 30.7 | 726 | 23.6 |

Example 6

Scale-Up of Animal-Free Fermentation Process to 300-L

To examine whether the animal component free fermentation process is scalable, 300-L batch fermentation is performed with MCDM/HSP-A. 4×1-mL vials from the Product Development Working Seed Bank (WSB) are inoculated into 220 ml WS/HSP-A/Glut in 1 L shake flask as listed in Table 19. When OD reaches about 2, seed cultures are transferred to second stage 3×2.8 L shake flasks, each containing 700 ml WS/HSP-A/Glut. At OD between 1.2 and 1.6, a 10% inoculum is used to inoculate seed culture from shake flask to 30 L fermentor with 20 L WS/HSP-A/Glut medium. Fermentation is controlled at pH 6.8±0.2, temperature 36±1° C., DO 30%, airflow at constant 15 L/min. At OD between 3–6, the 20 L seed culture is transferred to the 300-L fermentor.

TABLE 19

WS/HSP-A/Glut medium components

| Sodium phosphate, dibasic | 2.500 | g/L |
|---|---|---|
| HSP-A | 27.800 | g/L |
| Monosodium Glutamate | 5.000 | g/l |
| Potassium Chloride | 0.103 | g/L |
| Magnesium sulfate, crystals | 0.732 | g/L |
| L-Cysteine HCl Monohydrate | 0.023 | g/L |
| Dextrose | 11.250 | g/L |

300-L batch fermentation is controlled at pH 6.8±0.2, temperature 36±1° C., DO 30%. Control parameters are cascaded to maintain DO at 30%; agitation gradually increased to 280 rpm from 100; airflow gradually increased to 300 L/min from 75 L/min, and finally back pressure is gradually increased to 8 psi from 4 psi. If necessary, agitation is further gradually increased to maximum 500 rpm. The fermentation is harvested when hourly increase in OD slowed, indicating growth had reached stationary phase.

Table 20 lists seed culture OD and time for different seedtrain stages for serogroups A, C, and Y. It takes approximately 4–4.5 hours to attain transfer OD of about 2 in the first stage seed shake flask with WS/HSP-A/Glut medium; 1.75–2.5 hours to reach transfer OD of approximately 1.2 in the second stage flask; and 3–4 hours to attain a transfer OD of 3 in the 30-L fermentor. Table 21 summarizes the results from three 300-L runs, one each for groups A, C, and Y. Maximum OD 10.3 and PS 441 mg/L are observed for lot 085C22 group Y; maximum OD 10.2 and PS 653 mg/L for lot 087C42 group A; and maximum OD 8.3 and PS 272 mg/L for group C lot 087C103.

TABLE 20

Seed train OD and time

| N. meningtidis Lot No. | Sero-type | 1st Shake Flask Hours | OD | 2nd Shake Flask Hours | OD | 20L Seed Vessel Hours | OD |
|---|---|---|---|---|---|---|---|
| 087C22 | Y | 4.5 | 2.09 | 2.0 | 1.24 | 3.0 | 2.78 |
| 087C112 | W-135 | 4.5 | 2.03 | 2 | 1.15 | 3.75 | 2.63 |
| 087C129 | C | 4 | 2.45 | 1.75 | 1.51 | 3.75 | 3.01 |
| 087C137 | A | 4.5 | 2.18 | 2.75 | 1.35 | 3.25 | 2.66 |

TABLE 21

400 L fermentation OD and PS summary

| Lot No. | Serotype | Max. OD/Hr | Max. PS (mg/L)/Hr |
|---|---|---|---|
| 087C22 | Y | 10.3/6 | 441/7 |
| 087C112 | W-135 | 10.2/7 | 650/7 |
| 087C129 | C | 8.5/6 | 424/6 |
| 087C137 | A | 11.8/7 | 456/7 |

The embodiments provided herein are intended to illustrate specific embodiments of the present invention and are not intended to limit the scope of the invention. It is understood that alternative sources of salts, amino acids and the like may be used to substitute specific components described herein.

We claim:

1. A fermentation composition, comprising compounds in a ration, by weight, of 2.5±10% sodium phosphate, dibasic, 5–30+10% soy peptone, 5±10% monosodium glutamate, 0.103±10% potassium chloride, 0.732±10% magnesium sulfate, 0.016±10% L-cysteine, and 11.250±10% glucose, and wherein the composition does not comprise $NH_4Cl$.

2. The composition according to claim 1, wherein the composition is aqueous.

3. The composition according to claim 1, wherein the soy peptone is HSP-A®.

4. A fermentation composition, comprising compounds in a ration, by weight, of 10±10% glucose, 5–30±10% soy peptone, 5.8±10% sodium chloride, 1±10% potassium sulfate, 4±10% potassium phosphate, dibasic, 5–6±10% L-Glutamic Acid, 0.3±10% L-Arginine, 0.5±10% L-Serine, 0.23±10% L-Cysteine, 0.19±10% Magnesium Chloride, 0.021±10% calcium chloride, and 0.002±10% Ferrous Sulfate, and wherein the composition does not comprise $NH_4Cl$.

5. The composition according to claim 4, wherein the composition is aqueous.

6. The composition according to claim 4, wherein the soy peptone is HSP-A®.

7. A fermentation composition, comprising compounds in a ration, by weight, of 10±10% glucose, 5–30±10% soy peptone, 5.8±10% sodium chloride, 1±10% potassium sulfate, 4+10% potassium phosphate, dibasic, 0.19±10% magnesium chloride, 0.021±10% calcium chloride, and 0.002±10% ferrous sulfate, and wherein the composition does not comprise $NH_4Cl$.

8. The composition according to claim 7, wherein the composition is aqueous.

9. The composition according to claim 7, wherein the soy peptone is HSP-A®.

10. A method of fermenting Neisseria, comprising fermenting Neisseria in a fermentation composition wherein the fermentation composition does not comprise $NH_4Cl$, wherein the fermentation composition is according to claim 1, claim 4 or claim 7.

11. The method according to claim 10, wherein the fermentation composition is according to claim 1.

12. The method according to claim 10, wherein the fermentation composition is according to claim 4.

13. The method according to claim 10, wherein the fermentation composition is according to claim 7.

14. A method of fermenting Neisseria, wherein the Neisseria are fermented in multiple batches wherein at least on fermentation is in a fermentation composition of claim 1.

15. A method of fermenting Neisseria, wherein the Neisseria are fermented in multiple batches wherein at least one fermentation is in a fermentation composition of claim 4.

16. A method of fermenting Neisseria, wherein the Neisseria are fermented in multiple batches wherein at least one fermentation is in a fermentation composition of claim 7.

17. A method of fermenting Neisseria, comprising: inoculation a vial of Neisseria to a first flask containing a fermentation composition; cultivating the Neisseria in the first flask; transferring the Neisseria from the first flask to a plurality of second flasks containing a fermentation composition; fermenting the contents of the second flasks to a fed-batch fermentor containing a fermentation composition; fermenting the contents of the fed-batch fermentor with a fermentation composition, wherein at least one fermentation composition is of claim 4.

18. A method of fermenting Neisseria, comprising; inoculating a vial of Neisseria to a first flask containing a fermentation composition; cultivating the Neisseria in the fist flask; transferring the Neisseria from the first flask to a plurality of second flasks containing a fermentation composition; fermentation composition; fermenting the contents of the second flasks; transferring the contents of the second flasks to a fed-batch fermentor containing a fermentation composition; fermenting the contents of the fed-batch fermentor with a fermentation composition, wherein at least one fermentation composition is of claim 4.

19. A method of fermenting Neisseria, comprising: inoculating a vial of Neisseria to a first flask containing a fermentation composition; cultivating the Neisseria in the first flask; transferring the Neisseria from the first flask to a plurality of second flask containing a fermentation composition; fermenting the contents of the second flasks; transferring the contents of the second flasks to fed-batch fermentor containing a fermentation composition; fermenting the contents of the fed-batch fermentor with a fermentation composition, wherein at least one fermentation composition is of claim 7.

* * * * *